(12) United States Patent
Samejima et al.

(10) Patent No.: US 11,110,267 B2
(45) Date of Patent: Sep. 7, 2021

(54) ELECTRICAL TREATMENT APPARATUS, SYSTEM, AND COMPUTER-READABLE MEDIUM STORING PROGRAM

(71) Applicant: OMRON HEALTHCARE CO., LTD., Muko (JP)

(72) Inventors: Mitsuru Samejima, Kyoto (JP); Yui Watanabe, Kyoto (JP); Makoto Tabata, Kyoto (JP); Shozo Takamatsu, Kyoto (JP); Tetsuya Sato, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 83 days.

(21) Appl. No.: 16/458,348

(22) Filed: Jul. 1, 2019

(65) Prior Publication Data

US 2019/0321622 A1    Oct. 24, 2019

Related U.S. Application Data

(63) Continuation of application No. PCT/JP2017/041933, filed on Nov. 22, 2017.

(30) Foreign Application Priority Data

Jan. 4, 2017    (JP) .............................. JP2017-000151

(51) Int. Cl.
*A61N 1/02*    (2006.01)
*A61N 1/36*    (2006.01)
(Continued)

(52) U.S. Cl.
CPC ........... *A61N 1/025* (2013.01); *A61N 1/0492* (2013.01); *A61N 1/3603* (2017.08); *A61N 1/0408* (2013.01); *A61N 1/326* (2013.01)

(58) Field of Classification Search
None
See application file for complete search history.

(56) References Cited

U.S. PATENT DOCUMENTS 4,140,131 A * 2/1979 Dutcher ............... A61N 1/3706
607/29
5,709,712 A * 1/1998 Paul ..................... A61N 1/3708
607/27
(Continued)

FOREIGN PATENT DOCUMENTS

DE    697 21 332 T2    2/2004
JP    03-75066 A    3/1991
(Continued)

OTHER PUBLICATIONS

Official Communication issued in International Patent Application No. PCT/JP2017/041933, dated Feb. 6, 2018.
(Continued)

*Primary Examiner* — Brian T Gedeon
(74) *Attorney, Agent, or Firm* — Keating & Bennett, LLP

(57) ABSTRACT

An electrical treatment apparatus includes an electrode contactable with a body part, a voltage regulator to regulate a voltage applied to the electrode to provide electrical stimulation to the body part, and a control circuit to control the electrical treatment apparatus. While the control circuit is performing the treatment mode in which the voltage regulator is controlled to apply a voltage at a first voltage value corresponding to the treatment mode to the electrode, the control circuit controls the voltage regulator to switch a value of the voltage applied to the electrode from the first voltage value to a second voltage value and to thereafter switch the voltage value from the second voltage value to the first voltage value.

20 Claims, 7 Drawing Sheets

(51) Int. Cl.
  *A61N 1/04*   (2006.01)
  *A61N 1/32*   (2006.01)

(56) References Cited

U.S. PATENT DOCUMENTS

| | | | |
|---|---|---|---|
| 5,817,138 A | 10/1998 | Suzuki | |
| 7,774,056 B2* | 8/2010 | Torgerson | A61N 1/0529 607/2 |
| 2011/0054334 A1* | 3/2011 | Fischell | G16H 40/67 600/509 |
| 2017/0209693 A1 | 7/2017 | An et al. | |

FOREIGN PATENT DOCUMENTS

| | | |
|---|---|---|
| JP | 05-345036 A | 12/1993 |
| JP | 2001-507959 A | 6/2001 |
| JP | 2004-216031 A | 8/2004 |
| JP | 2014-004236 A | 1/2014 |
| JP | 2014-061110 A | 4/2014 |
| JP | 2015-000298 A | 1/2015 |
| JP | 2016-055178 A | 4/2016 |
| WO | 2015/199327 A1 | 12/2015 |

OTHER PUBLICATIONS

Official Communication issued in corresponding German Patent Application No. 112017006724.3, dated Mar. 30, 2021.

\* cited by examiner

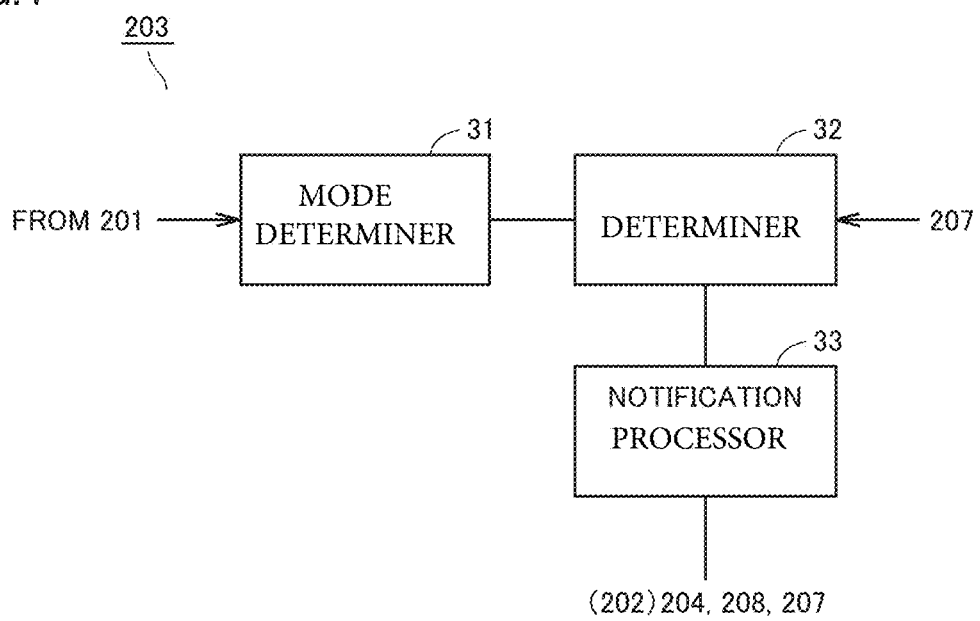

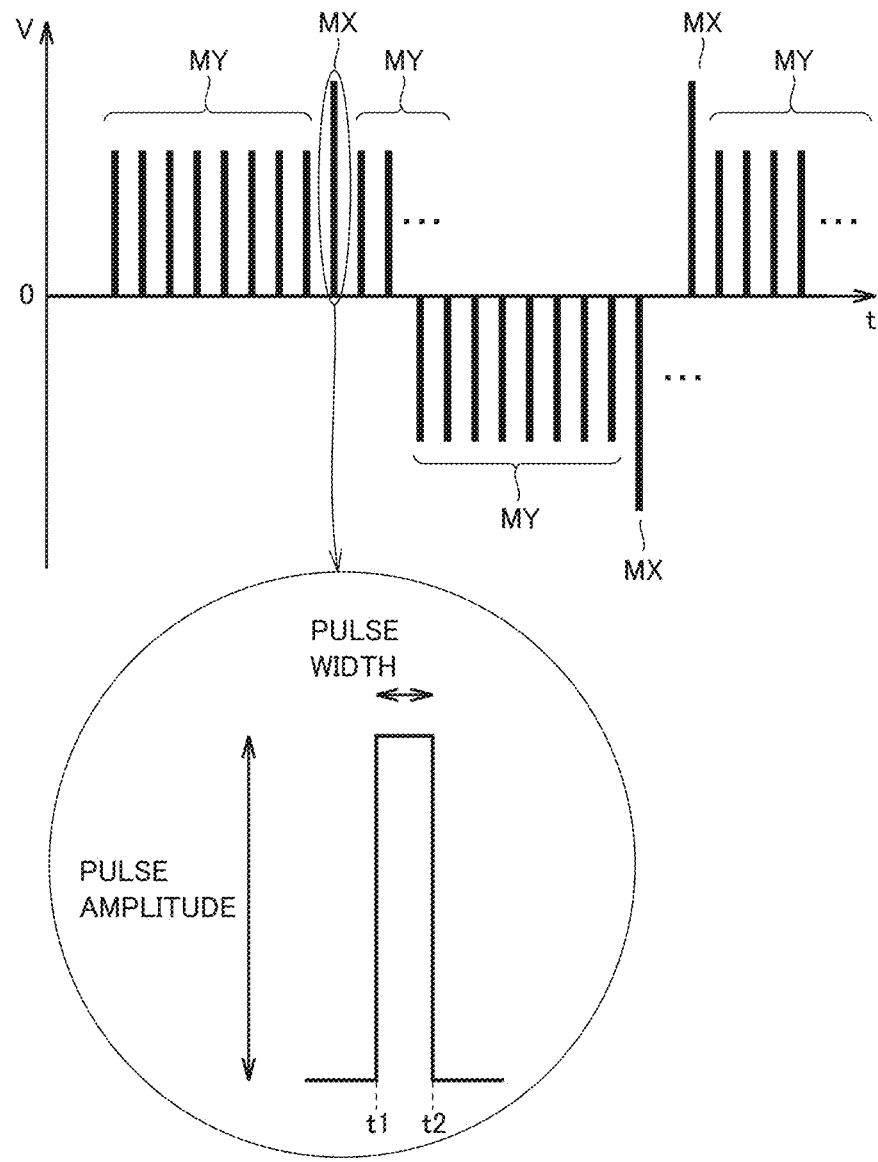

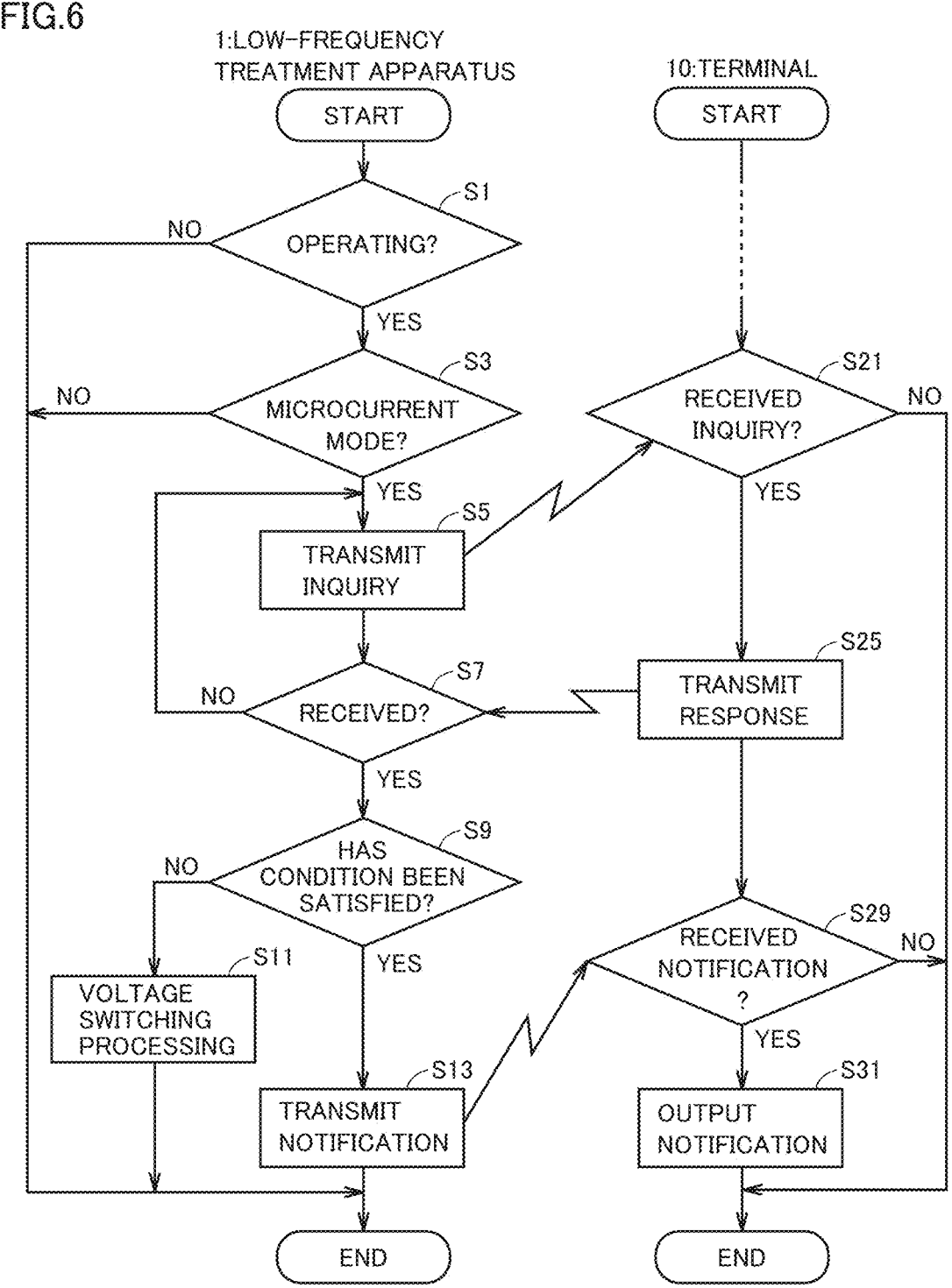

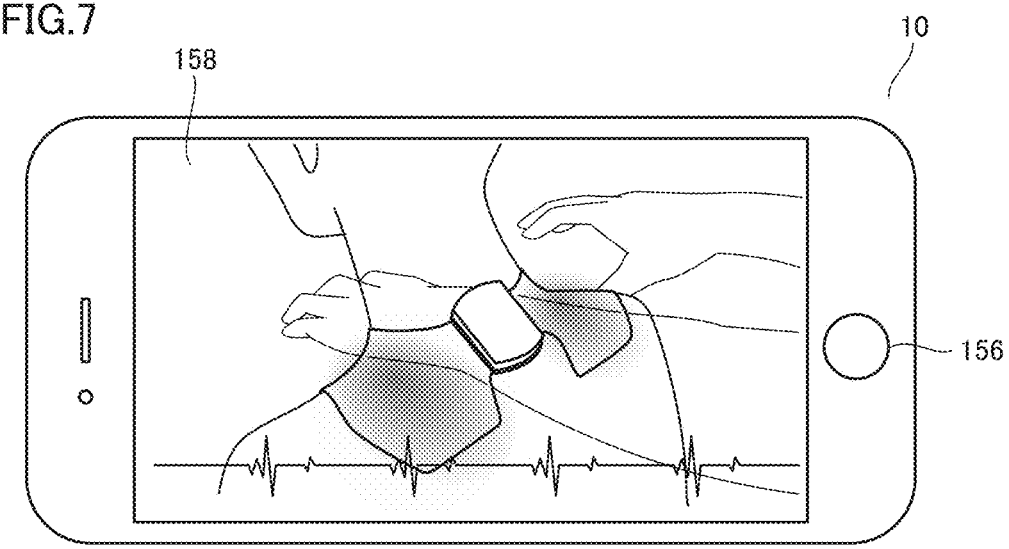

ELECTRICAL TREATMENT APPARATUS, SYSTEM, AND COMPUTER-READABLE MEDIUM STORING PROGRAM

CROSS REFERENCE TO RELATED APPLICATIONS

This application claims the benefit of priority to Japanese Patent Application No. 2017-000151 filed on Jan. 4, 2017 and is a Continuation Application of PCT Application No. PCT/JP2017/041933 filed on Nov. 22, 2017. The entire contents of each application are hereby incorporated herein by reference.

BACKGROUND OF THE INVENTION

1. Field of the Invention

The present disclosure relates to an electrical treatment apparatus, a system, and a computer-readable medium storing a program, and particularly to an electrical treatment apparatus, a system, and a computer-readable medium storing a program configured or programmed to control a voltage to be applied to an electrode to provide electrical stimulation to a body part.

2. Description of the Related Art

An electrical treatment apparatus configured to provide electrical stimulation to a body part of a user by outputting low-frequency pulses to the part through an electrode pad has been known as an electrical treatment apparatus. In using such an electrical treatment apparatus, a user desires to know a treatment mode such as magnitude of a current which flows to the body part.

Japanese Patent Laying-Open No. 2016-055178 discloses a configuration for showing on a display, a duration of electrical stimulation or time until end of electrical stimulation in an electrical stimulation treatment apparatus which uses a weak current.

A mode notification portion of Japanese Patent Laying-Open No. 2015-000298 outputs mode information on a frequency of a current which flows to a pad by means of an LED based on a mode notification signal. The mode information notifies a user of a low-frequency treatment mode set at that time.

According to Japanese Patent Laying-Open No. 2014-061110, an audio circuit connected to a contact portion with a negative electrode terminal of a main body being interposed outputs voice and sound in accordance with variation in direct current through a speaker and gives a notification about a state of treatment through voice and sound.

A potential treatment apparatus in Japanese Patent Laying-Open No. 2014-004236 has a subject recognize that the subject is being treated as the subject holds a detector and brings the detector closer to a first electrode to generate low-frequency waves (hum) to thereby vary intensity of light or a volume of buzzer sound.

Japanese Patent Laying-Open No. 5-345036 discloses a configuration capable of achieving not only a function for vascular enlargement by generating high-frequency electromagnetic field but also a hyperthermic effect resulting from far infrared rays emitted by far infrared ceramics excited by high-frequency pulses.

According to above-described related art, information on a treatment mode is output through a display, an LED, or an audio output (a speaker). In recent years, however, a manner of use in which electrical stimulation is provided to a body while a subject performs daily activities with an electrical treatment apparatus being worn under clothing has been proposed. In such an example where a display, an LED, or an audio output is integrally attached to the electrical treatment apparatus, it is difficult for a user to check the information because such a component is located under the clothing. Alternatively, when mode information is shown on a display separate from the electrical treatment apparatus, the user has to be present at a location from which information on the display is viewable, which makes usability poor.

SUMMARY OF THE INVENTION

Example embodiments of the present invention provide electrical treatment apparatuses, systems, and computer-readable media each storing a program capable of providing a notification about a treatment mode that is excellent in usability.

An electrical treatment apparatus according to an example embodiment of the present disclosure includes an electrode to be brought in contact with a body part, a voltage regulator to regulate a voltage applied to the electrode to provide electrical stimulation to the body part, and a controller configured or programmed to control the electrical treatment apparatus. The controller includes a notification processor configured or programmed to provide a notification about a treatment mode. The notification processor is configured or programmed to control, while the controller is performing the treatment mode in which the voltage regulator is controlled to apply a voltage at a first voltage value corresponding to the treatment mode to the electrode, the voltage regulator to switch a value of the voltage applied to the electrode from the first voltage value to a second voltage value and to thereafter switch the value of the voltage from the second voltage value to the first voltage value.

Preferably, the electrical treatment apparatus further includes a communicator to communicate with a terminal. The terminal includes an output to output information received from the electrical treatment apparatus. The notification processor is configured or programmed to control the communicator to transmit to the terminal, a notification that the treatment mode is being performed.

Preferably, the controller further includes a determiner configured or programmed to determine whether or not a predetermined condition based on a signal received from the terminal is satisfied. The notification processor is configured or programmed to control the voltage regulator to switch the value of the voltage applied to the electrode from the first voltage value to the second voltage value and to thereafter switch the value of the voltage from the second voltage value to the first voltage value when the predetermined condition is not satisfied.

Preferably, the notification processor is configured or programmed to control the communicator to transmit the notification to the terminal when the predetermined condition is satisfied.

Preferably, the predetermined condition includes a condition that intensity of the reception signal is equal to or greater than a threshold value.

Preferably, the terminal includes the output to output the information received from the electrical treatment apparatus. The signal received from the terminal includes a status signal indicating whether or not the output is in an information output allowable state. The predetermined condition includes a condition that the status signal included in the received signal indicates the information output allowable state.

Preferably, a length of time from switching of the value of the voltage applied to the electrode from the first voltage value to the second voltage value until subsequent switching of the value of the voltage from the second voltage value to the first voltage value is variable.

Preferably, intensity of electrical stimulation provided to the body part by applying the voltage at the second voltage value is higher than intensity of electrical stimulation provided to the body part by applying the voltage at the first voltage value.

Preferably, the electrical treatment apparatus is a low-frequency treatment apparatus.

A system according to another aspect of an example embodiment of the present disclosure includes an electrical treatment apparatus and a terminal to output information received from the electrical treatment apparatus. The electrical treatment apparatus includes an electrode to be brought into contact with a body part, a voltage regulator to regulate a voltage applied to the electrode to provide electrical stimulation to the body part, and a controller configured or programmed to control the electrical treatment apparatus. The controller includes a notification processor configured or programmed to provide a notification about a treatment mode. The notification processor is configured or programmed to control, while the controller is performing the treatment mode in which the voltage regulator is controlled to apply a voltage at a first voltage value corresponding to the treatment mode to the electrode, the voltage regulator to switch a value of the voltage applied to the electrode from the first voltage value to a second voltage value and to thereafter switch the value of the voltage from the second voltage value to the first voltage value.

According to yet another aspect of an example embodiment of the present disclosure, a non-transitory computer readable medium includes a program that causes a computer to perform a method of controlling an electrical treatment apparatus including an electrode to be brought in contact with a body part and a voltage regulator to regulate a voltage applied to the electrode to provide electrical stimulation to the body part, and the method includes performing a treatment mode to control the voltage regulator to apply a voltage at a first voltage value corresponding to the treatment mode to the electrode and providing a notification about the treatment mode. The providing a notification about the treatment mode includes controlling the voltage regulator to switch a value of the voltage applied to the electrode from the first voltage value to the second voltage value and to thereafter switch the value of the voltage from the second voltage value to the first voltage value while the treatment mode is being performed.

The above and other elements, features, steps, characteristics and advantages of the present invention will become more apparent from the following detailed description of the preferred embodiments with reference to the attached drawings.

BRIEF DESCRIPTION OF DRAWINGS

FIG. 4 is a diagram showing a functional configuration of low-frequency treatment apparatus 1 according to an example embodiment of the present disclosure.

FIG. 5 is a diagram showing a treatment waveform MY in a "microcurrent mode" and a waveform MX for providing a notification according to an example embodiment of the present disclosure.

FIG. 6 is a flowchart of processing according to an example embodiment of the present disclosure.

FIG. 7 is a diagram showing exemplary representation according to an example embodiment of the present disclosure.

DETAILED DESCRIPTION OF THE PREFERRED EMBODIMENTS

Figure 1:
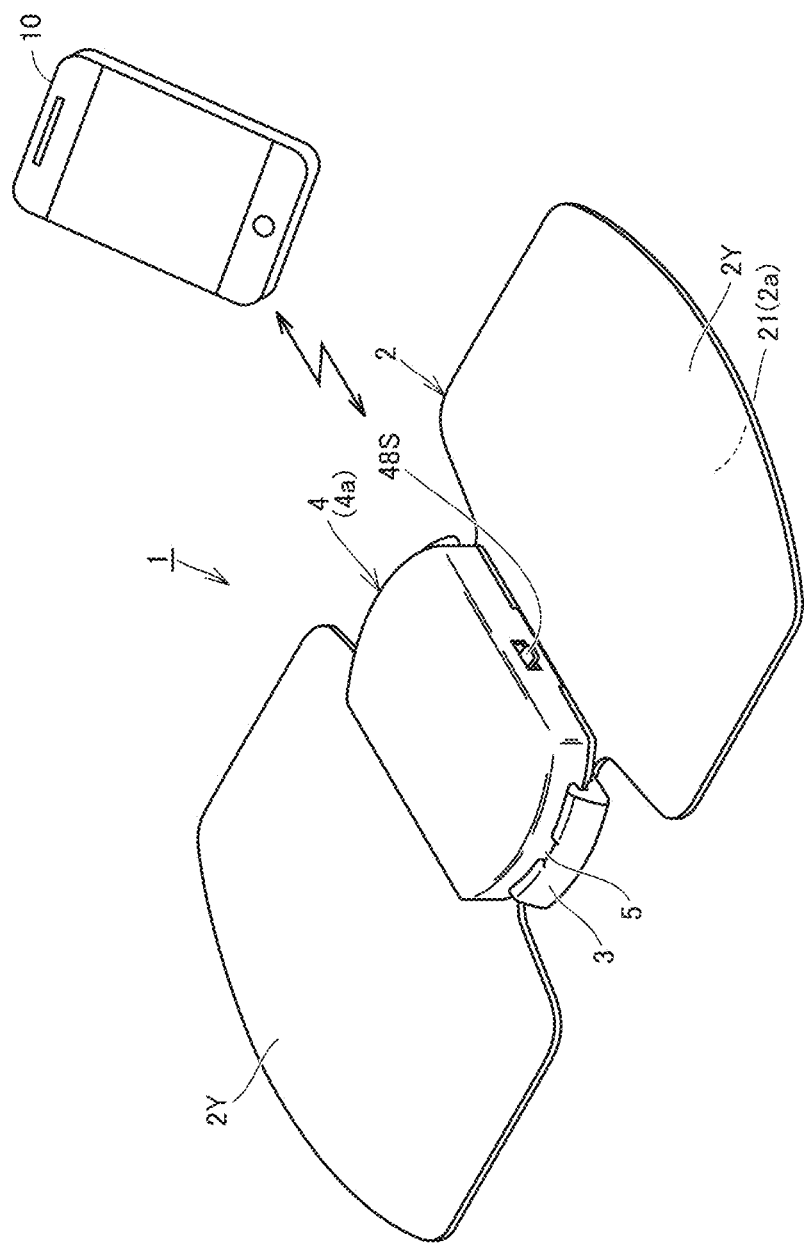
FIG. 1 is a diagram showing an appearance of a low-frequency treatment apparatus 1 according to an example embodiment of the present disclosure in association with a terminal 10.

Example embodiments of the present disclosure will be described below with reference to the drawings. The same elements and corresponding elements have the same reference characters allotted and redundant description may not be repeated.

First Example Embodiment

FIG. 1 is a diagram showing an appearance of a low-frequency treatment apparatus 1 according to an example embodiment of the present disclosure in association with a terminal 10. Low-frequency treatment apparatus 1 represents one example of an "electrical treatment apparatus." Terminal 10 represents one example of a "terminal" which communicates with low-frequency treatment apparatus 1. Though a smartphone (a multi-functional portable telephone) is shown by way of example of terminal 10, limitation to the smartphone is not intended and another terminal such as a foldable portable telephone, a tablet terminal, a personal computer (PC), or a personal digital assistance (PDA) may be used.

Referring to FIG. 1, low-frequency treatment apparatus 1 is what is called a cordless low-frequency treatment apparatus and includes a pad 2, a holder 3, and a main body portion 4.

Pad 2 represents one example of an "electrode" to be brought in contact with a body part. Pad 2 is preferably in a form of a sheet and attached as being in contact with a body part of a user, more specifically, a body part to be treated. A conductive layer 2a is provided on a surface (a lower surface) of a body-side portion 21 opposed to the body, of an outer surface of pad 2. Pad 2 is stuck to the skin of the user by using conductive gel or the like and a pulse current at a frequency in accordance with a treatment mode is supplied to the user through conductive layer 2a.

Pad 2 includes an attachment portion (not shown) and a treatment portion 2Y. The attachment portion is held by holder 3. Holder 3 is arranged in the attachment portion as being positioned. Treatment portion 2Y is provided on outer sides on the left and right of the attachment portion and conductive layer 2a is exposed at body-side portion 21 of treatment portion 2Y. Conductive layer 2a is exposed also at the surface opposed to main body portion 4 and the exposed portion implements an electrode.

Since pad 2 is consumable, pad 2 is attachable to and removable from main body portion 4 at the time of replacement. In the present example embodiment, as holder 3 holds pad 2, holder 3 and pad 2 are integrated with each other. Main body portion 4 is attachable to and removable from pad 2 and holder 3. Though pad 2 is replaced together with holder 3, holder 3 may be reused as necessary.

As shown in FIG. 1, main body portion 4 includes a case 4a substantially in a shape of a parallelepiped as an exterior. An engagement portion 5 is provided between case 4a and holder 3, and main body portion 4 (case 4a) is removably attached to holder 3 via engagement portion 5. Main body portion 4 is provided with a switch 48S operated by a user to control low-frequency treatment apparatus 1. Main body portion 4 includes a display (not shown) to output information on an operating state or the like of low-frequency treatment apparatus 1.

Main body portion 4 supplies a low-frequency pulse current to conductive layer 2a of pad 2 while it is attached to holder 3. Specifically, main body portion 4 includes a substrate, an electric circuit, and the like. The electric circuit includes various controllers to provide a low-frequency pulse current and is mounted on a surface of the substrate.

Figure 2:
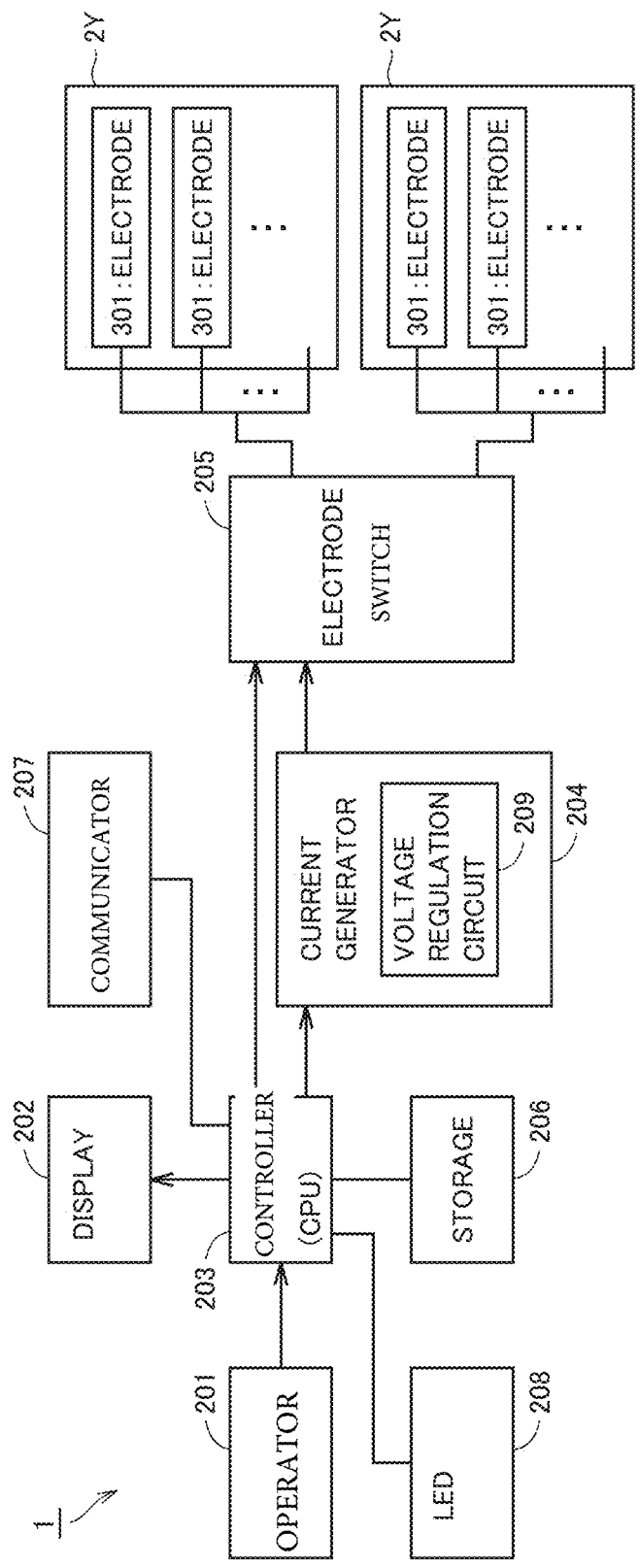
FIG. 2 is a diagram schematically showing an internal configuration of low-frequency treatment apparatus 1 according to a first example embodiment of the present disclosure.

FIG. 2 is a diagram schematically showing an internal configuration of low-frequency treatment apparatus 1 according to a first example embodiment of the present disclosure. Referring to FIG. 2, low-frequency treatment apparatus 1 includes as main components, an operator 201, a display 202, a controller 203 including one or more central processing unit (CPU), a current generator 204, an electrode switch 205, a storage 206, a communicator 207, and a light emitting diode (LED) 208. Though not shown, low-frequency treatment apparatus 1 includes a power supply which supplies electric power to each component. For example, an alkaline dry cell may be used as the power supply. The power supply generates a drive voltage to be supplied to each component by stabilizing a voltage of the cell.

Controller 203 typically includes a central processing unit (CPU) or a multi-processing unit (MPU). Controller 203 functions as a control circuit which controls an operation of each component in low-frequency treatment apparatus 1 by reading and executing a program stored in storage 206.

Storage 206 is implemented by a random access memory (RAM), a read-only memory (ROM), or a flash memory. Storage 206 stores a program executed by controller 203 or data used by controller 203.

Operator 201 includes, for example, switch 48S and various switches to accept an operation input from a user to low-frequency treatment apparatus 1. When the user operates operator 201, controller 203 accepts operation contents and controls each component in accordance with accepted operation contents.

Communicator 207 includes communication circuitry such as an AD (analog-digital) converter, a modulation circuit and a demodulation circuit to communicate with terminal 10. Communicator 207 includes a circuit which detects reception intensity (in a unit of decibel) of a signal received from terminal 10.

Current generator 204 outputs a current (which is also referred to as a "treatment current" below) which flows to a body part (more specifically, a body part to be treated) of a user through pad 2. Current generator 204 includes a boost circuit, a voltage regulation circuit 209, and an output circuit.

The boost circuit boosts a power supply voltage to a prescribed voltage. Voltage regulation circuit 209 regulates a voltage boosted by the boost circuit to a voltage at a value corresponding to intensity of electrical stimulation set by a user. Specifically, in low-frequency treatment apparatus 1, a type of a treatment mode can be set by operating operator 201. Regulation of electrical stimulation can be set for each type of the treatment mode. Controller 203 accepts an operation to set a treatment mode (that is, intensity of electrical stimulation) through operator 201 and controls current generator 204 (more specifically, voltage regulation circuit 209) to regulate a voltage to a value corresponding to intensity of electrical stimulation indicated by accepted operation contents.

The output circuit of current generator 204 generates a treatment waveform (a pulse waveform) in accordance with the treatment mode based on the voltage regulated by voltage regulation circuit 209 and outputs the treatment waveform to (the electrode of) pad 2. Specifically, when the user performs an operation to change the treatment mode or intensity of electrical stimulation through operator 201, a control signal in accordance with the operation contents is output from controller 203 to the output circuit of current generator 204. The output circuit generates a treatment waveform in accordance with the control signal.

Low-frequency treatment apparatus 1 includes a plurality of types of treatment modes. Examples of the treatment mode include various modes of "kneading", "tapping", and "pushing". The output circuit of current generator 204 generates a low-frequency treatment current in accordance with a control signal from controller 203. A pulse short in pulse width, for example, of approximately 100 μsec., preferably is used as a pulse having a waveform for treatment using the generated pulse current. A maximum value of a pulse amplitude is set, for example, to approximately 100 V. By varying a waveform (including a polarity, an interval, and a sequence) of the pulse, various types of stimulation such as "kneading", "tapping", "pushing", and "rubbing" can be created. By varying an amplitude or a width of a pulse, "intensity" (intensity of electrical stimulation) can be adjusted, and by varying a cycle of appearance of a group of pulses, a "speed" can be adjusted. Since conventionally well-known waveforms can be used, detailed description of specific waveforms will not be repeated. An alternating current (AC) instead of a pulse current may be used as the treatment current.

In the first example embodiment, regardless of a condition of the body or a state (dry or wet) of a body part with which an electrode is brought in contact, constant or substantially constant intensity of electrical stimulation is given. Therefore, low-frequency treatment apparatus 1 measures a biological impedance and determines an amplitude or a width of a pulse described above based on the measured biological impedance. Since a well-known method can be used as a method of measuring a biological impedance, description thereof will not be repeated.

Controller 203 generates a current control signal in accordance with designated treatment mode, intensity, and speed and sends the signal to current generator 204. Current generator 204 generates a low-frequency treatment current by modulation or amplification based on the current control signal. This single system line current is then distributed to electrodes 301 by electrode switch 205 and output to the body of a user through those electrodes 301. Muscles are electrically stimulated by the treatment current which flows between the pads and the muscles repeat contraction and relaxation. A treatment effect as in massaging is obtained.

A plurality of electrodes 301 of which conduction can be switched are provided for each pad 2 (more specifically, treatment portion 2Y) according to the present example embodiment and electrode switch 205 can switch between conduction and disconnection of one or more electrodes 301 in accordance with a switch signal from controller 203 while a low-frequency current is output from current generator 204. The low-frequency current is distributed to one electrode 301 or a plurality of electrodes 301 in a conducting state and output to the body through conducting electrode(s) 301.

Figure 3:
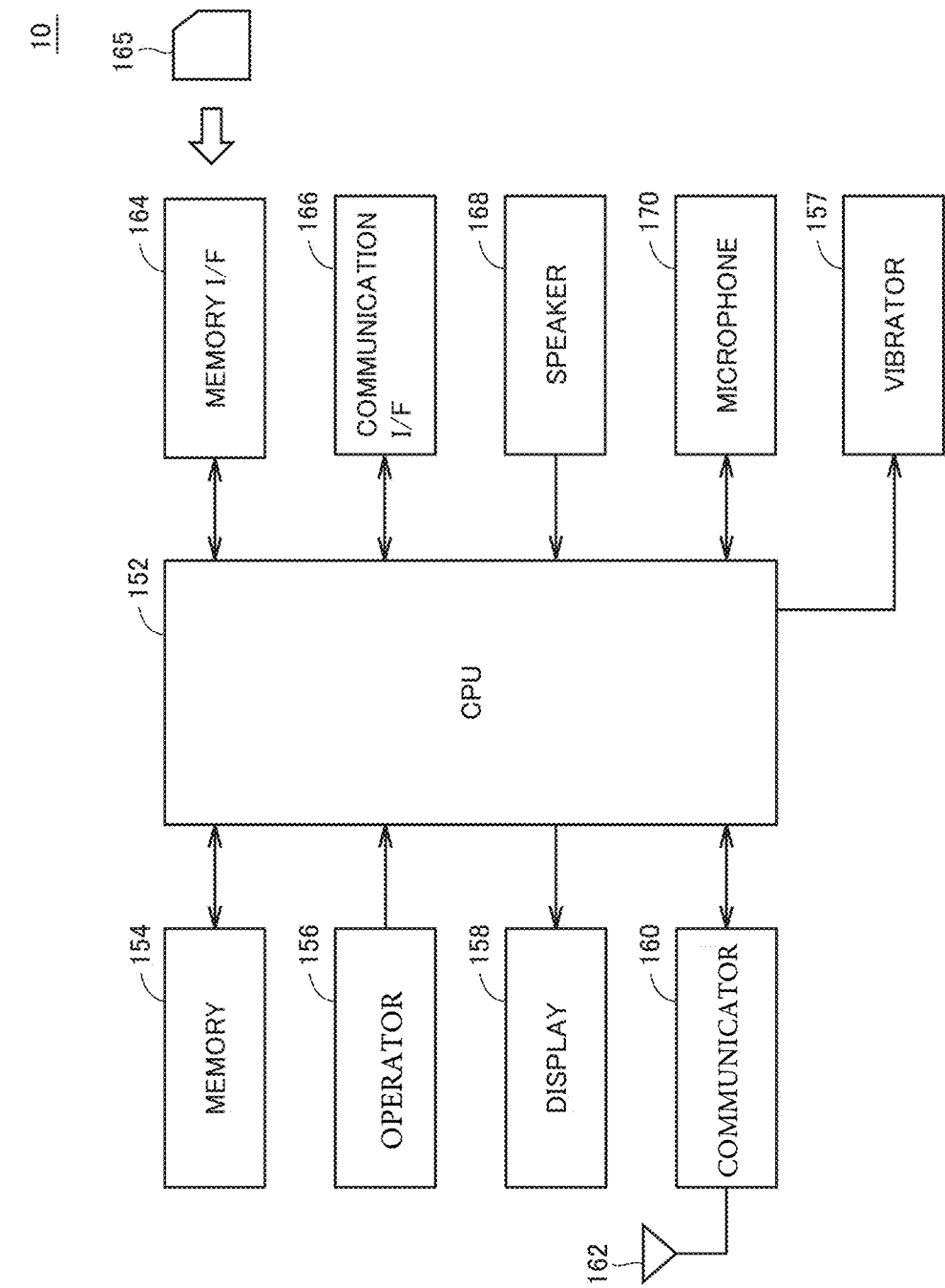
FIG. 3 is a block diagram showing one example of a hardware configuration of terminal 10 according to an example embodiment of the present disclosure.

FIG. 3 is a block diagram showing one example of a hardware configuration of terminal 10 according to the present example embodiment. Referring to FIG. 3, terminal 10 includes as main components, a CPU 152, a memory 154, an operator 156 to accept an operation by a user, a display 158 which shows information, a communicator 160, a memory interface (I/F) 164, a communication interface (I/F) 166, a speaker 168, a microphone 170, and a vibrator 157 to vibrate terminal 10.

CPU 152 functions as a controller which controls an operation by each component of terminal 10 by reading and executing a program stored in memory 154.

Memory 154 is implemented by a random access memory (RAM), a read-only memory (ROM), or a flash memory. Memory 154 stores a program executed by processor 152 or data used by processor 152.

Though operator 156 is implemented, for example, by a touch panel, it may include a button or the like. The operator may be provided as a touch panel display in which operator 156 and display 158 are integrated.

Communicator 160 is connected to a mobile communication network through an antenna 162 and transmits and receives a signal for wireless communication. Terminal 10 can thus communicate with another communication apparatus through a mobile communication network such as long term evolution (LTE).

Memory interface 164 reads data or a program from an external storage medium 165 and outputs the data or the program to CPU 152. Memory interface 164 has data from CPU 152 stored in external storage medium 165.

Communication interface (I/F) 166 is a communication interface to exchange various types of data between terminal 10 and low-frequency treatment apparatus 1 and implemented by an adapter, a connector, or the like. In the present preferred embodiment, Bluetooth® low energy (BLE) is adopted as a communication scheme. The communication scheme may be a wireless communication scheme by using wireless local area network (LAN).

A notification about a mode of treatment by low-frequency treatment apparatus 1 according to the first example embodiment will now be described. Low-frequency treatment apparatus 1 has a treatment mode in which a low-frequency treatment current flows (which is also called a microcurrent mode below).

By way of the background of the present example embodiment, in the microcurrent mode, a current that flows is weak. Therefore, intensity of electrical stimulation felt by a user is generally low and a user is less likely to realize that the user is being treated in the microcurrent mode. Therefore, the user desires to confirm that low-frequency treatment apparatus 1 is actually operating or that the user is being treated in the microcurrent mode.

With such a background, in the first example embodiment, controller 203 outputs via an output a notification that the microcurrent mode is being performed. A manner of output of the notification includes representation by display 202, turn-on of LED 208, transmission of a notification to terminal 10, and variation in voltage applied to the electrode.

When terminal 10 receives a notification from low-frequency treatment apparatus 1, it outputs the notification by representation of information on display 158, audio output from speaker 168, or vibration of vibrator 157, or by combination thereof.

In the first example embodiment, the notification is output by varying a voltage applied to the electrode. Specifically, in the microcurrent mode, a voltage at a first voltage value for the microcurrent mode is applied to the electrode. In such a microcurrent mode, to provide the notification described above, the voltage applied to the electrode is switched to a voltage at a large second voltage value which is not used in the microcurrent mode (which is also called voltage switching processing below). When switching to the voltage at the second voltage value, the user can feel relatively high intensity of electrical stimulation. The user can confirm that the microcurrent mode is being performed by feeling the intensity of electrical stimulation.

A treatment current at the first voltage value is, for example, of the order of microampere, whereas a current at the second voltage value is of the order of milliampere.

FIG. 4 is a diagram showing a functional configuration of low-frequency treatment apparatus 1 according to the first example embodiment. FIG. 4 shows a functional configuration of controller 203 to provide a notification that the "microcurrent mode is being performed" above. A function of each functional unit is mainly implemented by execution of a program by controller 203.

Referring to FIG. 4, controller 203 includes a mode determiner 31 that determines a type of a treatment mode selected by a user based on contents of an operation by the user accepted by operator 201, a determiner 32 which determines whether or not a predetermined condition is satisfied (met) based on a signal received from terminal 10, and a notification processor 33. Notification processor 33 performs processing to output a notification about a treatment mode determined by mode determiner 31 to a destination in accordance with a result of determination by determiner 32. Notification processor 33 controls at least one of display 202, current generator 204, LED 208, and communicator 207 for outputting a notification.

In the first example embodiment, when mode determiner 31 determines that the treatment mode has been set to the "microcurrent mode," controller 203 performs the "microcurrent mode."

When mode determiner 31 determines that the treatment mode has been set to the "microcurrent mode," determiner 32 determines whether or not a condition defined as the predetermined condition that intensity of a signal received from terminal 10 is equal to or greater than a threshold value is satisfied. In the first example embodiment, when terminal 10 is located near low-frequency treatment apparatus 1, intensity of the received signal is equal to or greater than the threshold value, that is, determiner 32 determines that the condition above is satisfied. In contrast, when intensity of the received signal is smaller than the threshold value in such an example that terminal 10 is remotely located, determiner 32 determines that the condition is not satisfied.

When determiner 32 determines that the predetermined condition is satisfied (that is, terminal 10 is located nearby), notification processor 33 controls communicator 207 to transmit to terminal 10, a notification that the "microcurrent mode" is being performed. When determiner 32 determines that the predetermined condition is not satisfied (that is, when terminal 10 is not located nearby), notification processor 33 performs voltage switching processing. Specifically, notification processor 33 controls current generator 204 (more specifically, voltage regulation circuit 209) to switch a value of a voltage to be applied to the electrode from the first voltage value to the second voltage value.

Thus, when intensity of the received signal is equal to or greater than the threshold value, that is, when terminal 10 is located near a user, terminal 10 can receive a notification transmitted from low-frequency treatment apparatus 1 and have, for example, display 158 show received information. Therefore, the user can confirm that the "microcurrent mode" is being performed based on information shown on display 158 of terminal 10 located nearby.

In contrast, when reception intensity is smaller than the threshold value, that is, when terminal 10 is not located near the user, the user is unable to observe information shown on display 158 of terminal 10, hear voice and sound output from speaker 168, or feel vibration of vibrator 157. In this case, as a result of voltage switching processing, the user can feel high intensity of electrical stimulation not experienced in the "microcurrent mode," and can confirm that the "microcurrent mode" is being performed.

When low-frequency treatment apparatus 1 includes the vibrator, a notification that a treatment in the "microcurrent mode" is being performed may be provided by vibration of the vibrator. A notification by vibration of low-frequency treatment apparatus 1 may be provided concurrently with voltage switching processing.

FIG. 5 is a diagram showing a treatment waveform MY in the "microcurrent mode" and a waveform MX to provide a notification according to the first example embodiment. In the "microcurrent mode," the output circuit of current generator 204 generates a treatment current at a low frequency in accordance with a control signal from controller 203. The treatment current at a low frequency is illustrated, for example, as waveform MY for treatment using a pulse current in FIG. 5. A short pulse having a pulse width, for example, of approximately 100 μsec. is preferably used as each pulse having treatment waveform MY. A maximum value of a pulse amplitude is set, for example, to approximately 100 V. By varying a polarity, an interval, or a sequence of pulses, various types of treatment waveforms such as "kneading," "tapping," "pushing", and "rubbing" in the "microcurrent mode" can be created.

In FIG. 5, a voltage at the first voltage value in the "microcurrent mode" corresponds to magnitude of an amplitude of treatment waveform MY, and a voltage at the second voltage value to provide a notification corresponds to magnitude of an amplitude of waveform MX. Referring to FIG. 5, waveform MX is greater in pulse amplitude than treatment waveform MY. As a current having waveform MX larger in pulse amplitude thus flows during treatment with a weak current (relatively low in intensity of electrical stimulation) in the "microcurrent mode," a user can feel higher intensity of electrical stimulation. The user can similarly feel higher intensity of electrical stimulation also by increasing a pulse width instead of a pulse amplitude.

During the treatment in the "microcurrent mode," controller 203 controls current generator 204 such that waveform MX is inserted as appropriate between treatment waveforms MY. Specifically, controller 203 controls current generator 204 (more specifically, voltage regulation circuit 209) to switch a value of a voltage applied to the electrode from the first voltage value to the second voltage value (time t1 in FIG. 5) and thereafter (time t2 in FIG. 5) to switch the value of the voltage from the second voltage value to the original first voltage value while the "microcurrent mode" is being performed.

A length of time (that is, a pulse width of waveform MX) from switching of the value of the voltage applied to the electrode from the first voltage value to the second voltage value (time t1 in FIG. 5) until subsequent switching of the value of the voltage from the second voltage value to the first voltage value (time t2 in FIG. 5) is variable. Though a pulse signal having waveform MX is repeatedly input between treatment waveforms MY, a cycle of repetition may also be variable.

FIG. 6 is a flowchart of processing according to the first example embodiment. This flowchart shows processing in low-frequency treatment apparatus 1 and processing in terminal 10 in association with each other. A program in accordance with the flowchart of processing in low-frequency treatment apparatus 1 is stored in storage 206. Controller 203 reads the program from storage 206 and executes the read program. A program in accordance with the flowchart of processing in terminal 10 is stored in memory 154. CPU 152 reads the program from memory 154 and executes the read program.

Referring to FIG. 6, controller 203 determines whether or not low-frequency treatment apparatus 1 is operating (step S1). When the controller determines that the low-frequency treatment apparatus is not operating (NO in step S1), a series of processing ends. When the controller determines that the low-frequency treatment apparatus is operating (YES in step S1), mode determiner 31 determines whether or not the treatment mode has been set to the "microcurrent mode" based on contents of an operation from operator 201 (step S3).

When mode determiner 31 determines that the treatment mode is not the "microcurrent mode" (NO in step S3), the series of processing ends. When the mode determiner determines that the treatment mode has been set to the "microcurrent mode" (YES in step S3), controller 203 transmits an inquiry to terminal 10 through communicator 207 (step S5).

In terminal 10, CPU 152 determines whether or not it has received the inquiry through communication interface (I/F) 166 (step S21). When CPU 152 determines that it has received no inquiry (NO in step S21), a series of processing ends. When the CPU determines that it has received the inquiry (YES in step S21), it transmits a response to low-frequency treatment apparatus 1 through communication interface (I/F) 166 (step S25).

In low-frequency treatment apparatus 1, controller 203 determines whether or not it has received a response from terminal 10 (step S7). When the controller determines that it has received no response (NO in step S7), the process returns to step S5 and subsequent processing is repeated.

When controller 203 determines that it has received a response (YES in step S7), determiner 32 determines whether or not the predetermined condition based on a reception signal has been satisfied (step S9). Specifically, whether or not a condition that intensity of the reception signal is equal to or greater than a threshold value is satisfied is determined. When it is determined that the condition is not satisfied (NO in step S9), notification processor 33 performs the voltage switching processing described above to provide a notification that the "microcurrent mode" is being performed (step S11). When it is determined that the condition is satisfied (YES in step S9), notification processor 33 controls communicator 207 to transmit to terminal 10, a notification that the "microcurrent mode" is being performed (step S13).

In terminal 10, CPU 152 determines whether or not it has received a notification from low-frequency treatment apparatus 1 through communication interface (I/F) 166 (step S29). When the CPU determines that the notification has not been received (NO in step S29), the series of processing ends. When the CPU determines that the notification has been received (YES in step S29), CPU 152 controls display 158 to show the received notification, controls speaker 168 to provide audio output of the notification, or controls vibrator 157 to vibrate in a pattern of the notification (step S31).

According to the processing in FIG. 6, the user can confirm that the "microcurrent mode" is being performed based on information output from terminal 10 or intensity of electrical stimulation.

Though a notification that the "microcurrent mode" is being performed as the treatment mode is provided in the first example embodiment, a type of a treatment mode of which notification is given is not limited to the "microcurrent mode." Though only transmission of a notification to terminal 10 is performed in step S13 in FIG. 6, a notification by voltage switching processing may also be provided together.

FIG. 7 is a diagram showing exemplary representation according to the first example embodiment. In step S31 in FIG. 6, display 158 shows a notification that the "microcurrent mode" is being performed in low-frequency treatment apparatus 1, for example, through an image in FIG. 7. In the image in FIG. 7, a body part (for example, a shoulder) to which low-frequency treatment apparatus 1 is attached is shown in an upper portion and a waveform of a pulse signal (see FIG. 5) is schematically shown in a lower portion. Information shown in accordance with a notification is not limited to the image in FIG. 7.

In the first example embodiment, though intensity of a signal received from terminal 10 being equal to or greater than a threshold value is defined as the predetermined condition subjected to determination by determiner 32, limitation thereto is not intended. In a first modification of an example embodiment of the present disclosure, the predetermined condition may include a condition that a status signal included in a signal received from terminal 10 indicates an information output allowable state.

For example, a response transmitted from terminal 10 to low-frequency treatment apparatus 1 (step S25 in FIG. 6) includes a status signal indicating that the output is in an information output allowable state. The output includes display 158, speaker 168, and vibrator 157 of terminal 10. When the output is in an operation on state, a response transmitted from terminal 10 to low-frequency treatment apparatus 1 includes a status signal indicating the information output allowable state.

In the first modification of an example embodiment of the present disclosure, determiner 32 determines whether or not a condition that a status signal included in a reception signal indicates an information output allowable state is satisfied. When the determiner determines that the condition is not satisfied (NO in step S9 in FIG. 6), notification processor 33 performs the voltage switching processing described above to provide a notification that the "microcurrent mode" is being performed (step S11 in FIG. 6). When the determiner determines that the condition is satisfied (YES in step S9 in FIG. 6), notification processor 33 controls communicator 207 to transmit a notification that the "microcurrent mode" is being performed to terminal 10 (step S13 in FIG. 6).

Thus, a user can confirm that the "microcurrent mode" is being performed based on information output from terminal 10 or intensity of electrical stimulation also in the first modification.

The predetermined condition may be defined as combination of the condition of reception intensity in the first example embodiment and the condition of a state of the output in the first modification of an example embodiment of the present disclosure.

In the voltage switching processing in the first example embodiment, the second voltage value may be variable. For example, the second voltage value may be varied depending on a biological impedance measured in a body or a body part with which an electrode is in contact. When the voltage value is varied depending on a body part, a body part with which the electrode is in contact can be determined based on an acceleration component indicated by an output from an acceleration sensor in an example in which the acceleration sensor is provided in low-frequency treatment apparatus 1.

Second Preferred Embodiment

A method of providing a notification that the "microcurrent mode" is being performed described with reference to the flowchart above can also be provided as a program executed by a computer (CPU). In order to realize this method, the program is stored, for example, in storage 206 of low-frequency treatment apparatus 1. The program may be supplied by downloading from an external information processing apparatus (for example, terminal 10) via communicator 207 through a communication line to storage 206.

Terminal 10 also similarly stores such a program in memory 154. A program is downloaded from an external terminal to memory 154 via communicator 160. Alternatively, a program read from storage medium 165 through memory I/F 164 may be loaded (stored) in memory 154.

Such a program may be provided to low-frequency treatment apparatus 1 or terminal 10 as a program product recorded on a non-transitory computer-readable recording medium such as a flexible disc, a compact disc read only memory (CD-ROM), and a memory card which are not shown.

Controller 203 shown in FIG. 2 and/or CPU 152 shown in FIG. 3 can be implemented by circuitry including, but not limited to, at least one semiconductor integrated circuit such as at least one processor (e.g., a central processing unit (CPU)), at least one application specific integrated circuit (ASIC), and/or at least one field programmable gate array (FPGA). At least one processor can be configured or programmed, by reading one or more instructions from at least one machine readable tangible medium, to perform all or a portion of functions of controller 203 including such as mode determiner 31, determiner 32 and notification processor 33. Such a medium may take many forms, including, but not limited to, any type of magnetic medium such as a hard disk, any type of optical medium such as a compact disc (CD) and a digital versatile disc (DVD), any type of semiconductor memory such as a volatile memory and a non-volatile memory. The volatile memory may include a dynamic random access memory (DRAM) and a static random access memory (SRAM), and the nonvolatile memory may include a read only memory (ROM) and a non-volatile RAM (NVRAM).

According to the present disclosure, intensity of electrical stimulation provided to a body can be varied by switching a value of a voltage applied to an electrode while a treatment mode is being performed, and a notification about the treatment mode can be given in a manner excellent in usability.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An electrical treatment apparatus comprising:
   an electrode to be brought in contact with a surface of skin of a body part;
   a voltage regulator to regulate a voltage applied to the electrode to provide electrical stimulation to the body part; and
   a control circuit to control, while the control circuit is performing a treatment mode in which the voltage regulator is controlled to apply a voltage at a first voltage value corresponding to the treatment mode to the electrode, the voltage regulator to switch a value of the voltage applied to the electrode from the first voltage value to a larger second voltage value at which high intensity of electrical stimulation not used in the treatment mode is discernible and to thereafter switch the value of the voltage from the second voltage value to the first voltage value.

2. The electrical treatment apparatus according to claim 1, further comprising a communication circuit to communicate with a terminal, wherein
   the terminal includes an output circuit to output information received from the electrical treatment apparatus, and
   the control circuit controls the communication circuit to transmit to the terminal, a notification that the treatment mode is being performed.

3. The electrical treatment apparatus according to claim 2, wherein the control circuit:
   determines whether a predetermined condition based on a signal received from the terminal is satisfied; and
   controls the voltage regulator to switch the value of the voltage applied to the electrode from the first voltage value to the second voltage value and to thereafter switch the value of the voltage from the second voltage value to the first voltage value when the predetermined condition is not satisfied.

4. The electrical treatment apparatus according to claim 3, wherein the control circuit controls the communication circuit to transmit the notification to the terminal when the predetermined condition is satisfied.

5. The electrical treatment apparatus according to claim 4, wherein the predetermined condition includes a condition that intensity of the received signal is equal to or greater than a threshold value.

6. The electrical treatment apparatus according to claim 4, wherein
   the signal received from the terminal includes a status signal indicating whether the output circuit is in an information output allowable state; and
   the predetermined condition includes a condition that the status signal included in the received signal indicates the information output allowable state.

7. The electrical treatment apparatus according to claim 1, wherein a length of time from switching of the value of the voltage applied to the electrode from the first voltage value to the second voltage value until subsequent switching of the value of the voltage from the second voltage value to the first voltage value is variable.

8. The electrical treatment apparatus according to claim 1, wherein intensity of electrical stimulation provided to the body part by applying the voltage at the second voltage value is higher than intensity of electrical stimulation provided to the body part by applying the voltage at the first voltage value.

9. The electrical treatment apparatus according to claim 1, wherein the electrical treatment apparatus is a low-frequency treatment apparatus.

10. A system comprising:
    an electrical treatment apparatus; and
    a terminal to output information received from the electrical treatment apparatus;
    the electrical treatment apparatus including:
      an electrode to be brought in contact with a surface of skin of a body part;
      a voltage regulator to regulate a voltage applied to the electrode to provide electrical stimulation to the body part; and
      a control circuit to control, while the control circuit is performing a treatment mode in which the voltage regulator is controlled to apply a voltage at a first voltage value corresponding to the treatment mode to the electrode, the voltage regulator to switch a value of the voltage applied to the electrode from the first voltage value to a larger second voltage value at which high intensity of electrical stimulation not used in the treatment mode is discernible and to thereafter switch the value of the voltage from the second voltage value to the first voltage value.

11. A method for controlling an electrical treatment apparatus including an electrode to be brought in contact with a surface of skin of a body part and a voltage regulator to regulate a voltage applied to the electrode to provide electrical stimulation to the body part, the method comprising:
    performing a treatment mode to control the voltage regulator to apply a voltage at a first voltage value corresponding to the treatment mode to the electrode; and
    providing a notification that a treatment mode is being performed;
    the providing a notification including controlling the voltage regulator to switch a value of the voltage applied to the electrode from the first voltage value to a larger second voltage value at which high intensity of electrical stimulation not used in the treatment mode is discernible and to thereafter switch the value of the voltage from the second voltage value to the first voltage value while the electrical treatment apparatus is performing the treatment mode.

12. The method according to claim 11, wherein the electrical treatment apparatus further includes a communication circuit to communicate with a terminal, and the terminal includes an output circuit to output information received from the electrical treatment apparatus, wherein
    the method further comprises controlling the communication circuit to transmit to the terminal, a notification that the treatment mode is being performed.

13. The method according to claim 12, further comprising:
    determining whether a predetermined condition based on a signal received from the terminal is satisfied; and
    controlling the voltage regulator to switch the value of the voltage applied to the electrode from the first voltage value to the second voltage value and to thereafter switch the value of the voltage from the second voltage value to the first voltage value when the predetermined condition is not satisfied.

14. The method according to claim 13, further comprising controlling the communication circuit to transmit the notification to the terminal when the predetermined condition is satisfied.

15. The method according to claim 14, wherein the predetermined condition includes a condition that intensity of the received signal is equal to or greater than a threshold value.

16. The method according to claim 14, wherein
the signal received from the terminal includes a status signal indicating whether the output circuit is in an information output allowable state; and
the predetermined condition includes a condition that the status signal included in the received signal indicates the information output allowable state.

17. The method according to claim 11, wherein a length of time from switching of the value of the voltage applied to the electrode from the first voltage value to the second voltage value until subsequent switching of the value of the voltage from the second voltage value to the first voltage value is variable.

18. The method according to claim 11, wherein intensity of electrical stimulation provided to the body part by applying the voltage at the second voltage value is higher than intensity of electrical stimulation provided to the body part by applying the voltage at the first voltage value.

19. A non-transitory computer-readable medium storing a program executable by one or more processors to perform a method of controlling an electrical treatment apparatus including an electrode to be brought in contact with a surface of skin of a body part and a voltage regulator to regulate a voltage applied to the electrode to provide electrical stimulation to the body part, the method comprising:

performing a treatment mode to control the voltage regulator to apply a voltage at a first voltage value corresponding to the treatment mode to the electrode; and
providing a notification that a treatment mode is being performed;
the providing a notification including controlling the voltage regulator to switch a value of the voltage applied to the electrode from the first voltage value to a larger second voltage value at which high intensity of electrical stimulation not used in the treatment mode is discernible and to thereafter switch the value of the voltage from the second voltage value to the first voltage value while the electrical treatment apparatus is performing the treatment mode.

20. The computer-readable medium according to claim 19, wherein the electrical treatment apparatus further includes a communication circuit to communicate with a terminal, and the terminal includes an output circuit to output information received from the electrical treatment apparatus, wherein
the method further comprises:
controlling the communication circuit to transmit to the terminal, a notification that the treatment mode is being performed;
determining whether a predetermined condition based on a signal received from the terminal is satisfied; and
controlling the voltage regulator to switch the value of the voltage applied to the electrode from the first voltage value to the second voltage value and to thereafter switch the value of the voltage from the second voltage value to the first voltage value when the predetermined condition is not satisfied.

* * * * *